US009681852B2

(12) United States Patent
Vriezema et al.

(10) Patent No.: US 9,681,852 B2
(45) Date of Patent: Jun. 20, 2017

(54) MEDICAL DEVICES WITH COATINGS FOR ENHANCED ECHOGENICITY

(71) Applicant: ENCAPSON B.V., Enschede (NL)

(72) Inventors: Dennis Manuel Vriezema, Nijmegen (NL); Lee Ayres, Nijmegen (NL); David Asrian, Bemmel (NL); Johannes Antonius Opsteen, Nettetal (DE)

(73) Assignee: Encapson B.V., Enschede (NL)

( * ) Notice: Subject to any disclaimer, the term of this patent is extended or adjusted under 35 U.S.C. 154(b) by 0 days.

(21) Appl. No.: 14/440,034

(22) PCT Filed: Oct. 31, 2013

(86) PCT No.: PCT/NL2013/050779
§ 371 (c)(1),
(2) Date: Apr. 30, 2015

(87) PCT Pub. No.: WO2014/070012
PCT Pub. Date: May 8, 2014

(65) Prior Publication Data
US 2015/0351721 A1 Dec. 10, 2015

(30) Foreign Application Priority Data
Oct. 31, 2012 (EP) .................................. 12190924

(51) Int. Cl.
| | | |
|---|---|---|
| *A61B 1/00* | (2006.01) | |
| *A61M 29/00* | (2006.01) | |
| *A61B 17/32* | (2006.01) | |
| *A61B 17/29* | (2006.01) | |
| *A61M 25/10* | (2013.01) | |
| *A61M 16/04* | (2006.01) | |
| *A61L 31/08* | (2006.01) | |
| *A61L 31/10* | (2006.01) | |
| *A61L 31/12* | (2006.01) | |
| *A61L 31/18* | (2006.01) | |
| *A61B 8/08* | (2006.01) | |
| *A61B 17/3205* | (2006.01) | |
| *A61B 17/34* | (2006.01) | |
| *A61B 17/00* | (2006.01) | |
| *A61B 90/00* | (2016.01) | |

(52) U.S. Cl.
CPC ................ *A61B 8/481* (2013.01); *A61B 1/00* (2013.01); *A61B 17/29* (2013.01); *A61B 17/32056* (2013.01); *A61L 31/088* (2013.01); *A61L 31/10* (2013.01); *A61L 31/128* (2013.01); *A61L 31/18* (2013.01); *A61M 16/0472* (2013.01); *A61M 25/104* (2013.01); *A61M 29/00* (2013.01); *A61B 2017/00526* (2013.01); *A61B 2017/3413* (2013.01); *A61B 2090/3925* (2016.02); *A61F 2250/0096* (2013.01); *A61L 2400/12* (2013.01); *A61L 2420/02* (2013.01)

(58) Field of Classification Search
CPC ..... A61B 17/29; A61B 17/32056; A61B 1/00; A61B 2017/00526; A61B 2017/3413; A61B 2090/3925; A61B 8/481; A61F 2250/0096; A61L 2300/606; A61L 2300/622; A61L 2400/12; A61L 2420/02; A61L 29/085; A61L 29/14; A61L 29/16
See application file for complete search history.

(56) References Cited

U.S. PATENT DOCUMENTS

| | | |
|---|---|---|
| 4,401,124 A | 8/1983 | Guess et al. |
| 5,081,997 A | 1/1992 | Bosley, Jr. et al. |
| 5,201,314 A | 4/1993 | Bosley, Jr. et al. |
| 5,289,831 A | 3/1994 | Bosley |
| 5,648,095 A | 7/1997 | Illum et al. |
| 5,741,522 A | 4/1998 | Violante et al. |
| 5,776,496 A | 7/1998 | Violante et al. |
| 5,921,933 A | 7/1999 | Sarkis et al. |
| 6,193,951 B1 | 2/2001 | Ottoboni et al. |
| 6,327,671 B1 | 12/2001 | Menon |
| 6,506,156 B1 | 1/2003 | Jones et al. |
| 6,749,554 B1* | 6/2004 | Snow .................... A61L 29/085 600/3 |
| 2002/0151796 A1* | 10/2002 | Koulik ................. A61K 49/222 600/458 |
| 2004/0077948 A1 | 4/2004 | Violante et al. |
| 2005/0074406 A1 | 4/2005 | Couvillon et al. |
| 2009/0048537 A1 | 2/2009 | Lydon et al. |
| 2009/0081130 A1 | 3/2009 | Ottoboni et al. |
| 2009/0177114 A1 | 7/2009 | Chin et al. |
| 2009/0318746 A1 | 12/2009 | Thurmond, II et al. |
| 2010/0239505 A1* | 9/2010 | Reichl .................. A61B 8/0833 424/9.52 |
| 2014/0207000 A1* | 7/2014 | Vriezema ............... A61B 8/481 600/458 |

FOREIGN PATENT DOCUMENTS

| | | |
|---|---|---|
| EP | 0500023 A1 | 8/1992 |
| EP | 624342 A1 | 11/1994 |
| EP | 552924 A1 | 7/1998 |
| EP | 1118337 A2 | 7/2001 |
| WO | 9818387 A1 | 5/1998 |

(Continued)

OTHER PUBLICATIONS

Tavakoli et al (Paper 401 presented at Society of Plastics Engineers Annual Technical Meeting, SPE ANTEC 2001 Conference—Medical Plastics, May 6-10, 2001, Dallas, Texas, USA. Also presented at Spring Medical Device Technology Conference. Birmingham, UK, Feb. 16-17, 2000, The Welding Institute).*

(Continued)

*Primary Examiner* — Mark V Stevens
(74) *Attorney, Agent, or Firm* — TraskBritt, P.C.

(57) ABSTRACT

The disclosure provides medical devices comprising improved coatings for ultrasound detection, which provide optimal ultrasound images. Methods for preparing such devices are also provided.

**6 Claims, 11 Drawing Sheets
(11 of 11 Drawing Sheet(s) Filed in Color)**

(56) References Cited

FOREIGN PATENT DOCUMENTS

| WO | 9819713 A1 | 5/1998 |
|---|---|---|
| WO | 9848783 A1 | 11/1998 |
| WO | 0051136 A1 | 8/2000 |
| WO | 0066004 A1 | 11/2000 |
| WO | 2007088256 A1 | 8/2007 |
| WO | 2007089724 A2 | 8/2007 |
| WO | 2007089761 A2 | 8/2007 |
| WO | 2008148165 A1 | 12/2008 |
| WO | 2010059408 A2 | 5/2010 |
| WO | 2012148265 A1 | 11/2012 |
| WO | 2014070012 A1 | 5/2014 |

OTHER PUBLICATIONS

Couture et al., A Model for Reflectivity Enhancement Due to Surface Bound Submicrometer Particles, Ultrasound in Medicine and Biology, vol. 32, No. 8, pp. 1247-1255, 2006.
Baldelli P, Phelan N, Egan G. A novel method for contrast-to-noise ratio (CNR) evaluation of digital mammography detectors. Eur Radiol 2009; Abstract, 19(9): 2275-2285.
Vygon leaflet "A light in the dark," at least as early as Jul. 1, 2010.
Vygon leaflet "periphere nerveblockaden," Nov. 2011.
PCT International Search Report, PCT/NL2012/050276 dated Jun. 8, 2012.
PCT International Search Report, PCT/NL2013/050779 dated Jan. 7, 2014.
Song et al., Automated region detection based on the contrast-to-noise ratio in near-infrared tomography, Applied Optics, Abstract, vol. 43, No. 5, 2004, pp. 1053-1062.

\* cited by examiner

MEDICAL DEVICES WITH COATINGS FOR ENHANCED ECHOGENICITY

CROSS-REFERENCE TO RELATED APPLICATIONS

This application is a national phase entry under 35 U.S.C. §371 of International Patent Application PCT/NL2013/050779, filed Oct. 31, 2013, designating the United States of America and published in English as International Patent Publication WO 2014/070012 A1 on May 8, 2014, which claims the benefit under Article 8 of the Patent Cooperation Treaty and under 35 U.S.C. §119(e) to European Patent Application Serial No. 12190924.6, filed Oct. 31, 2012.

TECHNICAL FIELD

The disclosure relates to the fields of medicine, physics and biotechnology.

BACKGROUND

In order to precisely locate a medical device such as, for instance, a needle or catheter inside a patient, ultrasound imaging is commonly used. Ultrasound imaging relies on the different ways in which sound waves are reflected from interfaces between substances. Ultrasound waves, with frequencies above the audible range of normal human hearing, typically from 20 kHz up to several gigahertz, are reflected in areas of density differences. In practice, a transducer is used that emits ultrasound waves, where after some of the reflected sound waves are detected by the transducer, which turns the vibrations into electrical pulses. These electrical pulses are processed and transformed into digital images.

The use of ultrasound imaging for medical devices is well known in the art. In order to enhance the quality of ultrasound images of medical devices, the surface of such a device is typically grooved or otherwise roughened, or an ultrasound coating is applied to at least part of the surface of the device. For instance, U.S. Pat. Nos. 5,289,831 and 5,081,997 describe echogenic medical devices having a surface with partially spherical indentations, or having a surface that is coated with spherically shaped particles, which scatter an ultrasound signal. International Patent Application WO 00/51136 describes the use of gas bubbles or metal particles for enhancing an ultrasound signal. The use of an echogenic material containing cavities or gas bubbles is also described in European Patent Application Serial No. EP 0624342, whereas International Patent Publications WO 98/18387 and WO 00/66004 describe medical instruments with bubble-generating means, which produce bubbles that are visible with ultrasound. Additionally, U.S. Patent Publication 2004/0077948 discloses an echogenic surface having structures entrapping gas, the entrapped gas causing the device to be ultrasonically visible.

U.S. Patent Publication 2005/0074406 describes an ultrasound coating containing membranes encapsulating a gas-filled core.

European Patent Application Serial No. EP 1118337 and U.S. Pat. No. 6,506,156 use an echogenic layer including a polymeric matrix with a plurality of void spaces, or glass microsphere particles, or both. U.S. Patent Publication 2009/0318746 describes lubricious echogenic coatings containing polymeric gas-/liquid-containing microparticles.

The use of roughened surfaces in order to enhance ultrasound visibility, however, involves an increased risk of discomfort for the patient since a roughened surface typically requires more force to move the device inside the patient's body and gives only a limited ultrasound visibility enhancement. The use of gas bubbles for improving ultrasound visibility has the disadvantage that it is difficult to control the concentration and size of the formed bubbles, leading to variations between coatings so that it is more difficult to obtain an optimized ultrasound imaging coating.

The use of echogenic particles is, therefore, preferred. Although various alternatives for ultrasound imaging with microparticles are available, it is advantageous to optimize the visibility (i.e., the accuracy) of the obtained ultrasound images. It is an object of this disclosure to provide such optimized coatings for ultrasound detection.

BRIEF SUMMARY

This disclosure provides the insight that an ultrasound image is optimized if at least 60% of the echogenic microparticles on a medical device have a diameter of between 10 and 45 μm and the density of the echogenic microparticles on the surface of the device is between 45 and 450 particles/mm$^2$. This is, for instance, apparent from the Examples: when particles with a diameter of between 10 and 45 μm are used, densities of between 45 and 450 particles/mm$^2$ provide a good visibility of the coated object, whereas lower or higher densities typically result in an image with an undesired deviation of the object size. Hence, the visibility of the object is best when densities of between 45 and 450 particles/mm$^2$ are used. In one preferred embodiment, a medical device is coated with echogenic particles, wherein at least 60% of the echogenic microparticles on a medical device have a diameter of between 22 and 45 μm and the density of the echogenic microparticles on the surface of the device is between 45 and 450 particles/mm$^2$ or, preferably, between 60 and 450 particles/mm$^2$.

As used herein, the visibility of an object as measured with ultrasound waves (also called the ultrasound visibility of an object) is defined as the accuracy with which the exact location of the object can be determined. Hence, visibility is proportional to the detail, or sharpness, of the obtained ultrasound image; the more detailed (sharper) the image, the better the user can locate the object, hence, the better the visibility of the object is. Interestingly, within the tested density ranges of between 0-1800 microspheres/mm$^2$, roughly corresponding to a surface packing of between 0.1 and 100% (a surface packing of 100% meaning that the highest possible hexagonal packing of spherical particles in a plane is achieved), it appears that objects with a surface density, and hence a reflectivity, above an optimal value lead to an overestimation of the object size under ultrasound. Hence, a higher reflectivity of ultrasound waves does not always result in a better visibility of a medical object. Contrary, the inventors have found that there is an optimal particle density, depending on the particle size. If the density becomes too high, the reflectivity will increase but the ability of a user to determine the exact location of a device will decrease because the ultrasound image will provide an overestimation of the object's size. The boundaries between the object and the environment become more vague, thereby decreasing the visibility of the object.

Without wishing to be bound by any theory, it is believed that as the number of particles on the surface increases, more ultrasound waves are scattered and returned to the transducer, resulting in an increase of reflectivity. At low particle densities, this increase in reflectivity increases the contrast-to-noise ratio of the signal of the coated device on the ultrasound machines screen, when compared to the signal of the surrounding medium, and it also increases the sharpness of the image, resulting in an improved ultrasound image on a screen. However, when the number of particles increases beyond an optimum point, the scattering is further increased, but the ultrasound image of the device becomes larger and less defined, leading to a less defined or less sharp image on the screen. This results in an overestimation of the size of the device, the appearance of ultrasound artifacts and a less-defined ultrasound image for a user. The result of this is a suboptimal image of the device and, hence, a decreased visibility.

This insight of the disclosure is in contrast with the general teaching in the art. For instance, Couture et al. (*Ultrasound in Medicine and Biology*, Vol. 32, No. 8, pp. 1247-1255, 2006) describes two mathematical models to predict the signal enhancement, or reflectivity, of microparticles on a surface. In the so-called layer model, the ultrasound particles are viewed as a continuous film covering the surface, with thickness corresponding to the particle diameter. According to this model, the reflectivity depends only on the film thickness (particle size) and not the particle density. In the second mathematical model proposed in Couture et al., at low surface concentration, the response to ultrasound radiation is modelled as the sum of the individual impulse response of all the particles, with all phases accounted for. From equation (5) on page 1249 of Couture et al., it is clear that according to this model, the reflectivity is proportional to the surface density of the ultrasound particles. Experimental data subsequently demonstrate that this is indeed the case for confluence fractions (surface packing) of up to 200% (which would roughly involve a particle density of up to 70,000 particles/mm$^2$ when the 5 µm particles of Couture et al. are used). For practical reasons, such high particle densities are normally not used on medical devices because it would become problematic to bind such high amounts of particles to a surface. Hence, Couture et al. only investigates the ultrasound reflectivity of echogenic particles and teaches a linear relationship between reflectivity and particle density up to 70,000 particles/mm$^2$. What is not realized in Couture et al., however, is the insight of this disclosure that the amount of reflectivity of the ultrasound particles does not always correlate to the visibility of the device in a patient. The disclosure provides the insight that too much reflectivity actually decreases the visibility. According to the disclosure, if the reflectivity is too high, then signal broadening and artifacts begin to appear and the ultrasound image seen by the user becomes less detailed (less sharp). In this case, the user will overestimate the size of the device and lose accuracy. The disclosure, therefore, provides coated medical devices with an improved ultrasound visibility. The diameters and the densities of the echogenic particles are adjusted in order to obtain an ultrasound image with improved visibility, meaning that the user is capable of accurately determining the position of the device inside a body.

Accordingly, the disclosure provides a medical device comprising a coating for ultrasound detection, the coating comprising microparticles that are visible with ultrasound, wherein the diameter of at least 60% of the microparticles on the medical device is between 10 and 45 µm and wherein the density of the microparticles on the surface of the medical device is between 45 and 450 particles/mm$^2$. Preferably, at least 65% of the microparticles on the medical device have a diameter of between 10 and 45 µm. More preferably, at least 70%, or at least 75%, of the microparticles on the medical device have a diameter of between 10 and 45 µm. More preferably, at least 80%, or at least 85%, or at least 90% of the microparticles on the medical device have a diameter of between 10 and 45 µm. Most preferably, at least 95% of the microparticles on the medical device have a diameter of between 10 and 45 µm. By using a high proportion of particles with a diameter between 10 and 45 µm, and a surface density of between 45 and 450 particles/mm$^2$, an optimal visibility of the medical device is obtained. In one particularly preferred embodiment, a medical device is provided that comprises a coating for ultrasound detection, wherein the coating comprises microparticles that are visible with ultrasound and wherein the diameter of at least 60% (preferably of at least 65%, 70%, 75%, 80%, 85%, 90% or 95%) of the microparticles on the medical device is between 22 and 45 µm and wherein the density of the microparticles on the surface of the medical device is between 45 and 450 particles/mm$^2$. In another preferred embodiment, the density is between 60 and 450 particles/mm$^2$.

In one embodiment, the diameter size of at least 60% of the individual particles is randomly distributed between 10 and 45 µm. In another embodiment, the diameter size of at least 60% of the individual particles is randomly distributed between 22 and 45 µm. It is also possible to use a mixture of particles with a higher proportion of particles with a diameter size between a more narrow sub-range. For instance, one preferred embodiment provides a medical device according to this disclosure, wherein the diameter of at least 60% of the microparticles on the medical device is between 22 and 27 µm. In such case, a particle density of between 150 and 450 particles/mm$^2$ provides an optimal visibility of the medical device and is, therefore, preferred. Even more preferably, the particle density is between 150 and 300 particles/mm$^2$ for optimal visibility.

One embodiment, therefore, provides a medical device comprising a coating for ultrasound detection, the coating comprising microparticles that are visible with ultrasound, wherein the diameter of at least 60% of the microparticles on the medical device is between 22 and 27 µm and wherein the density of the microparticles on the surface of the medical device is between 150 and 450 particles/mm$^2$, preferably between 150 and 300 particles/mm$^2$. Preferably, at least 65%, more preferably at least 70%, more preferably at least 75%, more preferably at least 80%, more preferably at least 85%, more preferably at least 90%, more preferably at least 95% of the microparticles on the medical device have a diameter between 22 and 27 µm.

In yet another embodiment, a medical device is coated with ultrasound particles, wherein the diameter of at least 60% of the microparticles on the medical device is between 27 and 32 µm. In this case, a particle density of between 70 and 450 particles/mm$^2$ is particularly preferred because a combination of a particle size of between 27 and 32 µm and a density of between 70 and 450 particles/mm$^2$ improves the visibility of a medical device inside a body. Even more preferably, the particle density is between 80 and 300 particles/mm$^2$ for optimal visibility.

Further provided is, therefore, a medical device comprising a coating for ultrasound detection, the coating comprising microparticles that are visible with ultrasound, wherein the diameter of at least 60% of the microparticles on the medical device is between 27 and 32 µm and wherein the density of the microparticles on the surface of the medical device is between 70 and 450 particles/mm$^2$, preferably between 80 and 300 particles/mm$^2$. Preferably, at least 65%, more preferably at least 70%, more preferably at least 75%, more preferably at least 80%, more preferably at least 85%, more preferably at least 90%, more preferably at least 95% of the microparticles on the medical device have a diameter between 27 and 32 µm.

In yet another embodiment, a medical device is coated with ultrasound particles, wherein the diameter of at least 60% of the microparticles on the medical device is between 32 and 38 µm. In this case, a particle density of between 45 and 225 particles/mm$^2$ is particularly preferred because a combination of a particle size of between 32 and 38 µm and a density of between 45 and 225 particles/mm$^2$ improves the visibility of a medical device inside a body. Further provided is, therefore, a medical device comprising a coating for ultrasound detection, the coating comprising microparticles that are visible with ultrasound, wherein the diameter of at least 60% of the microparticles on the medical device is between 32 and 38 µm and wherein the density of the microparticles on the surface of the medical device is between 45 and 225 particles/mm$^2$. Again, it is preferred that at least 65%, more preferably at least 70%, more preferably at least 75%, more preferably at least 80%, more preferably at least 85%, more preferably at least 90%, more preferably at least 95% of the microparticles on the medical device have a diameter between 27 and 32 µm. By using a high proportion of particles with the recited diameters and the recited surface densities, an optimal visibility of the medical device is obtained.

In yet another embodiment, a medical device is coated with ultrasound particles, wherein the diameter of at least 60% of the microparticles on the medical device is between 38 and 45 µm. In this case, a particle density of between 45 and 150 particles/mm$^2$ is particularly preferred because a combination of a particle size of between 38 and 45 µm and a density of between 45 and 150 particles/mm$^2$ improves the visibility of the device.

Further provided is, therefore, a medical device comprising a coating for ultrasound detection, the coating comprising microparticles that are visible with ultrasound, wherein the diameter of at least 60% of the microparticles on the medical device is between 38 and 45 µm and wherein the density of the microparticles on the surface of the medical device is between 45 and 150 particles/mm$^2$. Preferably, at least 65%, more preferably at least 70%, more preferably at least 75%, more preferably at least 80%, more preferably at least 85%, more preferably at least 90%, more preferably at least 95% of the microparticles on the medical device have a diameter between 38 and 45 µm.

The insight of this disclosure is in contrast with prior art teachings such as U.S. Pat. Nos. 5,289,831 and 5,081,997, which suggest that any amount of particles will provide a good image. U.S. Pat. No. 5,081,997 (column 6) and U.S. Pat. No. 5,289,831 (column 7) teach that glass microspheres with an outer diameter of about 5 microns is one acceptable option. Further, a general size range of 1-50 microns is given. U.S. Patent Publication 2009/0318746 discloses a preferred size range for echogenic particles of 0.1-30 µm. Furthermore, European Patent Application Serial No. EP 1118337 and U.S. Pat. No. 6,506,156 describe general size ranges of 20-200 µm and 50-150 µm. Hence, according to the prior art, the size of the echogenic particles is not very critical. Furthermore, no correlation is made between the sizes of the particles and optimal particle densities, as provided by the disclosure. It is this insight about the specific combinations of particle sizes and particle densities that improves the visibility of ultrasound images of medical devices in a body. The optimal density ranges and particle sizes as provided by this disclosure are not disclosed nor suggested in the prior art.

A medical device according to this disclosure can be coated with various kinds of microparticles that are visible with ultrasound. Such microparticles are known in the art. Suitable microparticles are, for instance, made from a material selected from the group consisting of polymers, ceramics, glasses, silicates, organic materials, metals and any combination thereof. In one embodiment, solid microparticles are used. Alternatively, gas-filled hollow microparticles are used. The gas preferably comprises air, nitrogen, a noble gas, a hydrocarbon and/or a fluorinated gas. In one embodiment, air-filled particles are used.

In one preferred embodiment, the echogenic microparticles are echogenic microspheres. In one embodiment, the microparticles are present on the surface of a medical device as a monolayer because this reduces the thickness and roughness of the surface, as compared to double layers and multilayers. A less roughened surface typically requires less force to move the device inside a patient's body. A thinner coating affects the properties of the medical device less.

Preferably, echogenic microparticles with a diameter between 10 and 45 µm or between 22 and 45 µm are used. This means that at least 60%, preferably at least 65%, preferably at least 70%, preferably at least 75%, preferably at least 80%, preferably at least 85%, preferably at least 90% and most preferably at least 95% of the particles have a diameter between 10 and 45 µm or between 22 and 45 µm. Hence, some variations are tolerated, as long as the majority of the particles have a diameter within the recited diameter range. Echogenic microparticles with a diameter between 10 and 45 µm are preferred for coating medical devices, because significantly smaller particles have a lower ultrasound scattering capacity so that echogenicity is often not sufficiently enhanced and the contrast-to-noise ratio is often too low, whereas significantly larger particles often result in a highly increased scattering effect and, therefore, an overestimation of the size of the medical device. Furthermore, with particles with a diameter of 45 µm or less, a coated medical device is typically sufficiently smooth to avoid discomfort for a subject, which would be due to resistance that is experienced when moving a device with a rough surface inside a subject's body.

A "medical device" is defined herein as any kind of device that can be used in an animal or human body. The medical device can preferably be inserted or implanted in the body. Preferably, such medical device is an instrument used in surgery, treatment and/or diagnosis. Surgical instruments are well known in the art. Non-limiting examples of medical devices include catheters, needles, stents, cannulas, tracheotomes, endoscopes, dilators, tubes, introducers, markers, stylets, snares, angioplasty devices, trocars and forceps. A medical device according to this disclosure is, therefore, preferably selected from the group consisting of catheters, needles, stents, cannulas, tracheotomes, endoscopes, dilators, tubes, introducers, markers, stylets, snares, angioplasty devices, fiducials, trocars and forceps.

As used herein, a coating for ultrasound detection comprises any coating that is tolerated by a human or animal body and that comprises microparticles that can be visualized, due to scattering of ultrasound waves. Typically, such coating comprises biocompatible materials that are non-toxic, hypoallergenic and stable.

An "ultrasound wave" (also called "an ultrasound signal" or "ultrasound") is defined as a sound pressure wave with a frequency above the audible range of normal human hearing. Typically, ultrasound waves have a frequency above 20 kHz. For imaging of medical devices, ultrasound waves with a frequency between 2 MHz and 50 MHz are preferably used.

As used herein, the term "ultrasound image" means any kind of visualization of an object using ultrasound waves. Typically, reflected ultrasound waves are converted into electrical pulses that are processed and transformed into digital images. Such images are embraced by the term "ultrasound image."

A "microparticle" is defined herein as a particle with a size below 1000 μm (preferably equal to or higher than 1 μm and lower than 1000 μm). Microparticles can have any shape, such as a regular shape (for instance, spherical, oval or cubical) or an irregular shape.

A "microsphere" is defined herein as an essentially spherical particle with a diameter lower than 1000 μm, preferably lower than 500 The term "essentially spherical" reflects the fact that the particles need not be perfectly spherical as long as the distances between the center and any point at the surface do not differ more than 50%, more preferably no more than 30%, from each other in at least 70%, preferably at least 80%, most preferably at least 90% of the particles.

A "monolayer," also called a "single layer," is defined herein as a one-particle thick layer of particles on the surface of a device, meaning that there is, on average, no more than one particle on an axis perpendicular to the surface of the device. Some variations in thickness of the layer are tolerated, as long as at least 70%, preferably at least 80%, most preferably at least 90% of the surface of a device is coated with a single layer of particles.

A "double layer" is defined herein as a two-particle thick layer of particles on the surface of a device, meaning that there is, on average, no more than two particles on an axis perpendicular to the surface of the device. Again, some variations in thickness of the layer are tolerated, as long as at least 70%, preferably at least 80%, most preferably at least 90% of the surface of a device is coated with a double layer of particles.

"Echogenic microparticles" are defined herein as microparticles that are able to reflect an ultrasound wave.

A diameter of a microparticle according to the disclosure is defined herein as the maximal size of the particle. The particle does not need to be exactly spherical although, in practice, essentially spherical particles are preferred.

A "microparticle" with a diameter between a given range is defined herein as a microparticle that has a diameter that lies within the recited range, including the lower and upper value of the range. For instance, a microparticle with a diameter between 10 and 45 μm may have a diameter of 10 μm, a diameter of 45 μm, or a diameter with a value anywhere within this range.

A "silicate" is defined herein as any compound comprising $SiO_2$ and/or $SiO_4$ groupings, or any salt derived from the silicic acids or from silica.

As used herein, the term "glass" refers to a solid material that exhibits a glass transition when heated toward the liquid state. Preferably, silica glass is used, which is an $SiO_2$-containing glass. Typically, soda-lime-silica glass is used, which is the most prevalent type of glass. It comprises $SiO_2$, sodium carbonate, calcium oxide, magnesium oxide and/or aluminium oxide. Other types of glasses can be used, such as, for instance, quartz, sodium borosilicate or other borosilicate glasses, lead oxide, and/or aluminosilicate.

The term "plastic" refers to organic polymers of high molecular mass. Non-limiting examples of plastics include poly(ether sulfone)s, polyisocyanates, polyurethanes, polytetrafluoroethylene, polymers or copolymers of N-vinyl-pyrrolidone (e.g., copolymers with butylacrylate), poly-(4-vinyl pyridine), polyacrylamide (e.g., poly(N-isopropylacrylamide)s), poly(amido-amine)s, poly(ethylene imine)s, block copolymers of ethylene oxide and propylene oxide (e.g., a poly(ethylene oxide-block-propylene oxide) or poly(ethylene oxide-block-propylene oxide-block-ethylene oxide)), block copolymers of styrene (e.g., a poly(styrene-block-isobutylene-block-styrene) or poly(hydroxystyrene-block-isobutylene-block-hydroxystyrene)), polydialkylsiloxanes, polysaccharides, polystyrenes, polyacrylates, polyalkylacrylates (e.g., a polymethylmethacrylate or a poly (2-hydroxyethylmethacrylate)), polyalkanes (e.g., polyethylene, polypropylene and polybutadiene), poly(ether ketone)s (e.g., poly(ether ketone) or poly(ether ether ketone)), polyesters (e.g., poly(ethylene terephthalate), polyglycolides, poly(trimethylene terephthalate) or poly (ethylene naphthalate), poly(lactic acid), polycapralactone, poly(butylene terephthalate), polyamides (e.g., nylon-6,6, nylon-6, a polyphthalamide or a polyaramide), and one or more combinations of the above.

As used herein, the term "surface coverage" refers to the percentage of a surface that is covered by echogenic microparticles. The surface coverage is typically determined by dividing the added-up dimensions of microparticle-covered surface parts by the total dimension of the surface as a whole.

The term "surface density" is defined herein as the amount of particles per square millimeter of the surface of a device. In common practice, some non-significant variation between the actual density of a coated object and an indicated density value is typically allowed. For instance, a 5-10% difference is typically considered non-significant.

The term "reflectivity" as used herein typically refers to the fraction or amount of ultrasound waves returned from a surface or interface, e.g., to be received by an ultrasound transducer.

The term "contrast-to-noise ratio" (CNR) is defined herein as the difference between the reflection of a (the) echogenic particle(s) as described herein and the reflection of the surrounding tissue (background reflection). Methods for calculating CNRs are, for instance, disclosed in Song et al. (*Applied Optics*, Vol. 43, No. 5 (2004); 1053-1062) and in Baldelli et al. (*Eur. Radiol.* 19 (2009); 2275-2285).

In one preferred aspect, a medical device is provided that comprises a coating for ultrasound detection, the coating comprising microparticles that are visible with ultrasound, wherein the diameter of at least 60% of the microparticles on the medical device is between 38 and 45 μm and wherein the density of the microparticles on the surface of the medical device is lower than 150 particles/mm$^2$. It was found that ultrasound images obtained with medical devices that are coated with echogenic particles with a density that is higher than 150 particles/mm$^2$, wherein the diameter of at least 60% of the microparticles on the medical device is between 38 and 45 μm, are less accurate, because of the overestimation of the size of the device and the appearance of artifacts. This is, for instance, shown in Example 5 and FIG. 9: the right image is obtained with a coated device, whereby the diameter of at least 60% of the microparticles on the medical device is between 38 and 45 μm and the density of echogenic microparticles on the surface of the device is about 250 particles/mm$^2$, the middle image is obtained with a coated device with the same kind and size of particles, whereby the density of echogenic microparticles on the surface of the device is about 180 particles/mm$^2$ and the left image is obtained with a coated device with the same kind and size of particles, whereby the density of echogenic microparticles on the surface of the device is about 130 particles/mm$^2$. It is clear that the right image of FIG. 9 has a lower detail (sharpness), so that it is, for instance, more difficult for a surgeon to exactly locate the end or tip of such device. Moreover, a cloud can be seen at the left end of the device, which lowers the quality and accuracy of the obtained image even more. Furthermore, a comparison between the left image of FIG. 9 (coating with a density of echogenic particles of about 130 particles/mm$^2$) and the middle image of FIG. 9 (coating with a density of echogenic particles of about 180 particles/mm$^2$) shows that the detail (sharpness) and, hence, the visibility of the left image of FIG. 9 is better than the detail (sharpness) of the middle image of FIG. 9.

Again, contrary to expectations, this disclosure provides the insight that the presence of more echogenic microparticles, resulting in more reflectivity, does not always increase the visibility of a device. On the contrary, visibility is decreased if densities above an optimum value are used.

In one embodiment, a medical device according to this disclosure comprises a plastic surface. Non-limiting examples are plastics selected from the group consisting of polyurethane, polyvinyl chloride and silicones, and PEBAX®. Alternatively, a medical device according to this disclosure comprises a metal surface, such as, for instance, stainless steel, NITINOL™, chromium, gold, or platinum.

As stated before, suitable microparticles for a medical device according to the disclosure are, for instance, made from a material selected from the group consisting of polymers, ceramics, glasses, silicates, organic materials, metals and any combination thereof. Preferably, glass or silicate microparticles are used. In one particularly preferred embodiment, the microparticles are echogenic microspheres. The microparticles may be solid microparticles. Hollow microparticles are also suitable, in particular, gas-filled microparticles or microspheres such as gas-filled glass or silicate particles. In one embodiment, the particles are filled with air, nitrogen, a noble gas, a hydrocarbon and/or a fluorinated gas. Preferably, the particles are filled with air or a fluorinated gas.

In principle, any coating capable of applying microparticles to a medical device and that is suitable for in vivo use is suitable for a medical device according to the disclosure. Such coating is preferably non-toxic, hypo-allergenic and stable. A medical device according to the disclosure preferably comprises a coating that comprises a matrix material selected from the group of polymers, preferably wherein the polymer is selected from the group consisting of a poly(ether sulfone); a polyisocyanate; a polyurethane; a polytetrafluoroethylene; a polymer or copolymer of N-vinyl-pyrrolidone such as a copolymer with butylacrylate; a poly(4-vinyl pyridine); a polyacrylamide such as poly(N-isopropylacrylamide); a poly(amido-amine); a poly(ethylene imine); a block copolymer of ethylene oxide and propylene oxide such as a poly(ethylene oxide-block-propylene oxide) or a poly(ethylene oxide-block-propylene oxide-block-ethylene oxide); a block copolymer or styrene such as poly(styrene-block-isobutylene-block-styrene) or poly(hydroxystyrene-block-isobutylene-block-hydroxystyrene); a polydialkylsiloxane; a polysaccharide; a polystyrene, a polyacrylate, a polyalkane such as polyethylene, polypropylene or polybutadiene, a poly(ether ketone) such as poly(ether ketone), poly(ether ether ketone), polyesters such as poly(ethylene terephthalate), polyglycolide, poly(trimethylene terephthalate), poly(ethylene naphthalate), poly(lactic acid), polycapralactone, poly(butylene terephthalate), polyamides such as nylon-6,6, nylon-6, polyphthalamides or polyaramides, a polyalkylmethacrylate such as a polymethylmethacrylate, a poly(2-hydroxyethylmethacrylate), and combinations thereof, preferably selected from poly(ether sulfones), poly- urethanes, polyacrylates, polymethacrylates, polyamides, polycarbonates, and combinations thereof.

In one embodiment, a medical device according to the disclosure comprises a plastic tube. Such device, for instance, comprises a catheter.

Further provided are methods for preparing a medical device according to this disclosure. Methods for preparing echogenic coatings and for applying these coatings on medical devices are well known in the art. For instance, known techniques for preparing polymer microcapsules are solvent evaporation, coacervation, interfacial polymerization, spray drying and fluid bed coating. Glass microcapsules are, for instance, prepared using ultrasonic spray pyrolysis, sol-gel processing, liquid drop processing or electrodispersion precipitation. Subsequently, a medical device is, for instance, coated with the microparticles by dip coating, spray coating, pad printing, roller coating, printing, painting or inkjet printing.

Reference is, for instance, made to U.S. Pat. Nos. 5,289, 831, 5,921,933, and 6,506,156, to International Patent Publication WO 2007/089761 and to *Ultrasound in Medicine and Biology*, Vol. 32, No. 8, pp. 1247-1255, 2006, which describe methods for preparing echogenic particles and coatings. Such coating is preferably biocompatible, non-toxic, hypo-allergenic and stable. A medical device according to the disclosure preferably comprises a coating that comprises a matrix material listed hereinbefore, comprising echogenic microparticles according to this disclosure.

One aspect, therefore, provides a method for preparing a medical device comprising a coating for ultrasound detection, the coating comprising microparticles that are visible with ultrasound, wherein diameter of at least 60% of the microparticles on the medical device is between 10 and 45 μm and wherein the density of the microparticles on the surface of the medical device is between 45 and 450 particles/mm$^2$, the method comprising:

providing a medical device, and coating the device with microparticles that are visible with ultrasound, such that the diameter of at least 60% of the microparticles on the medical device is between 10 and 45 μm and the density of the microparticles on the surface of the medical device is between 45 and 450 particles/mm$^2$.

Preferably, at least 60%, more preferably at least 65%, more preferably 75%, more preferably at least 80%, more preferably at least 85%, more preferably at least 90%, more preferably at least 95% of the microparticles on the medical device have a diameter between 10 and 45 μm.

Also provided is a method for preparing a medical device comprising a coating for ultrasound detection, the coating comprising microparticles that are visible with ultrasound, wherein diameter of at least 60% of the microparticles on the medical device is between 22 and 45 μm and wherein the density of the microparticles on the surface of the medical device is between 45 and 450 particles/mm$^2$, the method comprising:

providing a medical device, and coating the device with microparticles that are visible with ultrasound, such that the diameter of at least 60% of the microparticles on the medical device is between 22 and 45 μm and the density of the microparticles on the surface of the medical device is between 45 and 450 particles/mm$^2$. In one preferred embodiment, the device is coated with microparticles that are visible with ultrasound, such that the diameter of at least 60% of the microparticles on the medical device is between 22 and 45 µm and the density of the microparticles on the surface of the medical device is between 60 and 450 particles/mm².

Preferably, at least 60%, more preferably at least 65%, more preferably 75%, more preferably at least 80%, more preferably at least 85%, more preferably at least 90%, more preferably at least 95% of the microparticles on the medical device have a diameter between 22 and 45 µm.

In one embodiment, the diameter size of at least 60% of the individual particles is randomly distributed between 10 and 45 µm. In another embodiment, the diameter size of at least 60% of the individual particles is randomly distributed between 22 and 45 µm. It is also possible to use a mixture of particles with a higher proportion of particles with a diameter size between a more narrow sub-range. For instance, one preferred embodiment provides a medical device according to this disclosure, wherein the diameter of at least 60% of the microparticles on the medical device is between 22 and 27 µm. In such case, a particle density of between 150 and 450 particles/mm² provides a particularly good visibility of the medical device and is, therefore, preferred. Even more preferred is a particle density of between 150 and 300 particles/mm².

One embodiment, therefore, provides a method for preparing a medical device comprising a coating for ultrasound detection, the coating comprising microparticles that are visible with ultrasound, wherein the diameter of at least 60% of the microparticles on the medical device is between 22 and 27 µm and wherein the density of the microparticles on the surface of the medical device is between 150 and 450 particles/mm², preferably between 150 and 300 particles/mm², the method comprising:
  providing a medical device, and
  coating the device with microparticles that are visible with ultrasound, such that the diameter of at least 60% of the microparticles on the medical device is between 22 and 27 µm and the density of the microparticles on the surface of the medical device is between 150 and 450 particles/mm², preferably between 150 and 300 particles/mm².

Preferably, at least 65%, more preferably at least 70%, more preferably at least 75%, more preferably at least 80%, more preferably at least 85%, more preferably at least 90%, more preferably at least 95% of the microparticles on the medical device have a diameter between 22 and 27 µm.

In yet another embodiment, a medical device is coated with ultrasound particles, wherein the diameter of at least 60% of the microparticles on the medical device is between 27 and 32 µm. In this case, a particle density of between 70 and 450 particles/mm² is particularly preferred because a combination of a particle size of between 27 and 32 µm and a density of between 70 and 450 particles/mm² improves the visibility of a device inside a body. Even more preferably, the particle density is between 80 and 300 particles/mm² for optimal visibility.

Further provided is, therefore, a method for preparing a medical device comprising a coating for ultrasound detection, the coating comprising microparticles that are visible with ultrasound, wherein the diameter of at least 60% of the microparticles on the medical device is between 27 and 32 µm and wherein the density of the microparticles on the surface of the medical device is between 70 and 450 particles/mm², preferably between 80 and 300 particles/mm², the method comprising:
  providing a medical device, and
  coating the device with microparticles that are visible with ultrasound, such that the diameter of at least 60% of the microparticles on the medical device is between 27 and 32 µm and the density of the microparticles on the surface of the medical device is between 70 and 450 particles/mm², preferably between 80 and 300 particles/mm².

Preferably, at least 65%, more preferably at least 70%, more preferably at least 75%, more preferably at least 80%, more preferably at least 85%, more preferably at least 90%, more preferably at least 95% of the microparticles on the medical device have a diameter between 27 and 32 µm.

In yet another embodiment, a medical device is coated with ultrasound particles, wherein the diameter of at least 60% of the microparticles on the medical device is between 32 and 38 µm. In this case, a particle density of between 45 and 225 particles/mm² is particularly preferred because a combination of a particle size of between 32 and 38 µm and a density of between 45 and 225 particles/mm² improves the visibility of a medical device inside a body. Further provided is, therefore, a method for preparing a medical device comprising a coating for ultrasound detection, the coating comprising microparticles that are visible with ultrasound, wherein the diameter of at least 60% of the microparticles on the medical device is between 32 and 38 µm and wherein the density of the microparticles on the surface of the medical device is between 45 and 225 particles/mm², the method comprising:
  providing a medical device, and
  coating the device with microparticles that are visible with ultrasound, such that the diameter of at least 60% of the microparticles on the medical device is between 32 and 38 µm and the density of the microparticles on the surface of the medical device is between 45 and 225 particles/mm².

Preferably, at least 65%, more preferably at least 70%, more preferably at least 75%, more preferably at least 80%, more preferably at least 85%, more preferably at least 90%, more preferably at least 95% of the microparticles on the medical device have a diameter between 32 and 38 µm.

In yet another embodiment, a medical device is coated with ultrasound particles, wherein the diameter of at least 60% of the microparticles on the medical device is between 38 and 45 µm. In this case, a particle density of between 45 and 150 particles/mm² is particularly preferred because a combination of a particle size of between 38 and 45 µm and a density of between 45 and 150 particles/mm² improves the visibility of the device even more.

Further provided is, therefore, a method for preparing a medical device comprising a coating for ultrasound detection, the coating comprising microparticles that are visible with ultrasound, wherein the diameter of at least 60% of the microparticles on the medical device is between 38 and 45 µm and wherein the density of the microparticles on the surface of the medical device is between 45 and 150 particles/mm², the method comprising:
  providing a medical device, and
  coating the device with microparticles that are visible with ultrasound, such that the diameter of at least 60% of the microparticles on the medical device is between 38 and 45 µm and the density of the microparticles on the surface of the medical device is between 45 and 150 particles/mm².

Preferably, at least 65%, more preferably at least 70%, more preferably at least 75%, more preferably at least 80%, more preferably at least 85%, more preferably at least 90%, more preferably at least 95% of the microparticles on the medical device have a diameter between 38 and 45 µm.

The disclosure is further illustrated by the following examples. These examples are not limiting the disclosure in any way, but merely serve to clarify the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Examples

Example 1

Commercially available solid glass microspheres (from Cospheric) with diameters ranging from 10 to 22 μm, 22 to 27 μm, 27 to 32 μm, 32 to 38 μm, 38 to 45 μm and 45 to 53 μm, all with a density of 2.5 g/mL, were mixed through a polyurethane coating matrix. The microspheres were added in different amounts in order to prepare mixtures containing 0.5 to 75.0 vol. % microspheres in the coating matrix. Subsequently, either 30- or 60-μm thick coating films were drawn on both glass and PEBAX® 6233 slides as substrates using a film applicator. The density of microspheres was determined to vary from 2 to 1831 particles/mm$^2$.

The coated substrates were measured by ultrasound using a 33 mm linear array probe operating in brightness-mode (B-mode) at 6 MHz. The substrates were placed under an approximate angle of 45 degrees inside a commercially available ultrasound phantom, which acted as the medium.

Figure 1:
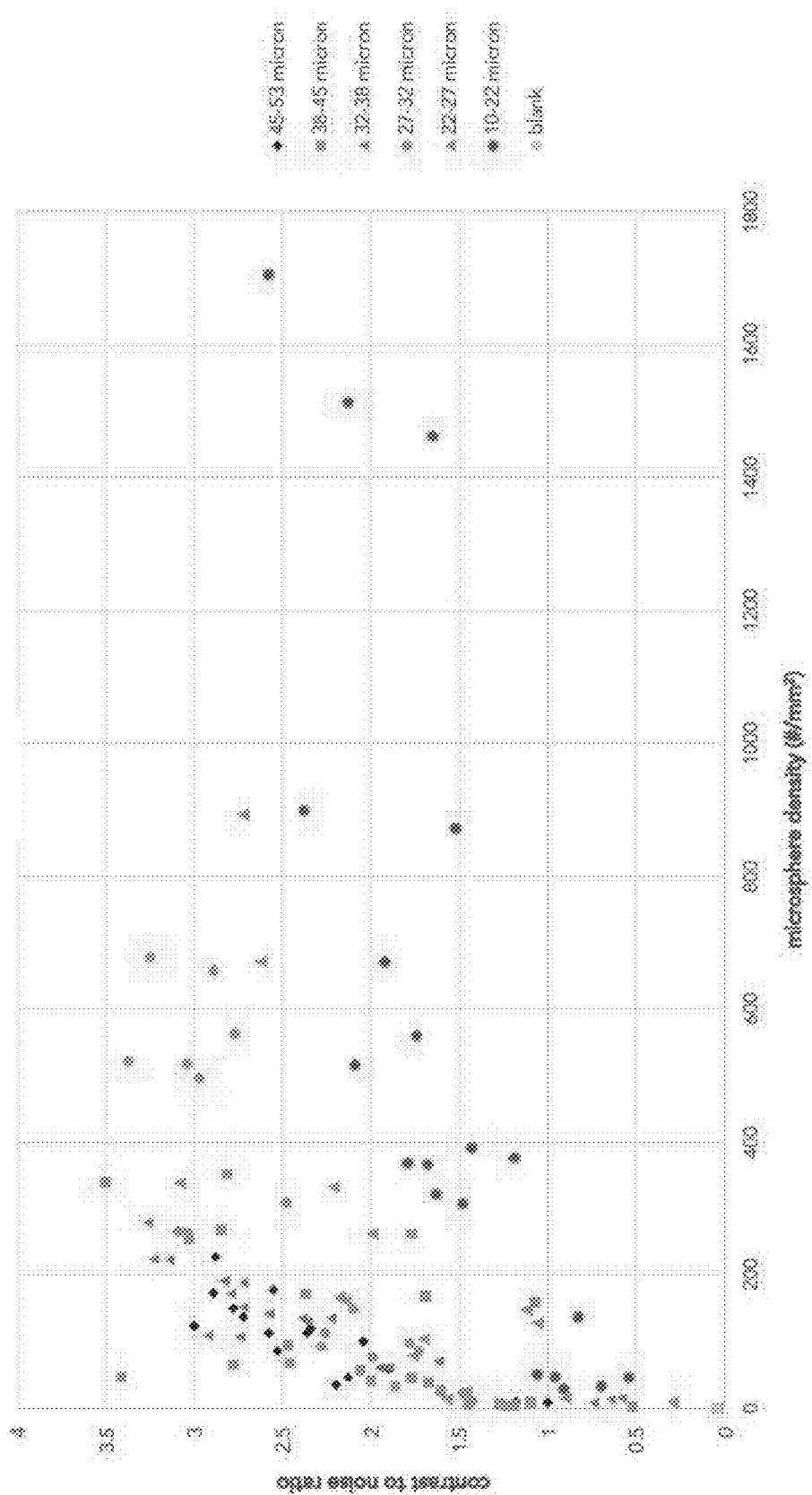
FIG. 1: Plot of the CNR against the microsphere density on the surface for different microsphere sizes.

From the recorded images, the contrast-to-noise ratio (CNR) was determined by comparing the average pixel intensity and standard deviation of the coated objects to the values obtained for the surrounding medium, according to:

$$CNR = \frac{P_{ROI} - P_{medium}}{\sqrt{\frac{\sigma_{ROI}^2 - \sigma_{medium}^2}{2}}}$$

where
$P_{ROI}$=average pixel intensity of region of interest
$P_{medium}$=average pixel intensity of medium
$\sigma_{ROI}$=standard deviation in region of interest
$\sigma_{medium}$=standard deviation in medium The determined CNRs were plotted against the microsphere density in particles/mm$^2$ (FIG. 1).

As can be seen in FIG. 1, the CNR approaches a value of approximately 3.5 with an increasing amount of microspheres on the surface. For the microspheres ranging from 10 to 22 μm, the maximum attainable CNR was approximately 2.5. Higher CNR values could not be obtained due to the fact that the complete surface is covered with glass microspheres. Adding a second layer of microspheres on top did not result in an increase of the CNR. Therefore, particles with a diameter between 22 and 45 μm are more preferred.

Example 2

Commercially available solid glass microspheres with diameters ranging from 10 to 22 μm, 22 to 27 μm, 27 to 32 μm, 32 to 38 μm, 38 to 45 μm and 45 to 53 μm, all with a density of 2.5 g/mL, were mixed through a polyurethane coating matrix. The microspheres were added in different amounts in order to prepare mixtures containing 1.0 to 75.0 vol. % microspheres in the coating matrix. Subsequently, either 30- or 60-μm thick marker bands of coating were drawn on glass slides using a film applicator. These marker bands were applied by masking the area that was required to be uncoated. The width of the marker bands was measured.

The coated substrates were measured by ultrasound using a 33 mm linear array probe operating in brightness-mode (B-mode) at 6 MHz. The substrates were placed under an approximate angle of 45 degrees inside a commercially available ultrasound phantom, which acted as the medium.

From the recorded images, the width of the marker bands as visible under ultrasound was determined. The under or overestimation of the width of the marker band under ultrasound is expressed as:

$$US\ \text{estimation error} = \frac{L_{US} - L_{actual}}{L_{actual}} \times 100\%$$

where
$L_{US}$=the width of the ultrasound signal stemming from the marker band
$L_{actual}$=the actual width of the marker band In principle, an US estimation error of below 10% is considered acceptable. Preferably, the US estimation error is between 0 and about 5%.

Figure 2:
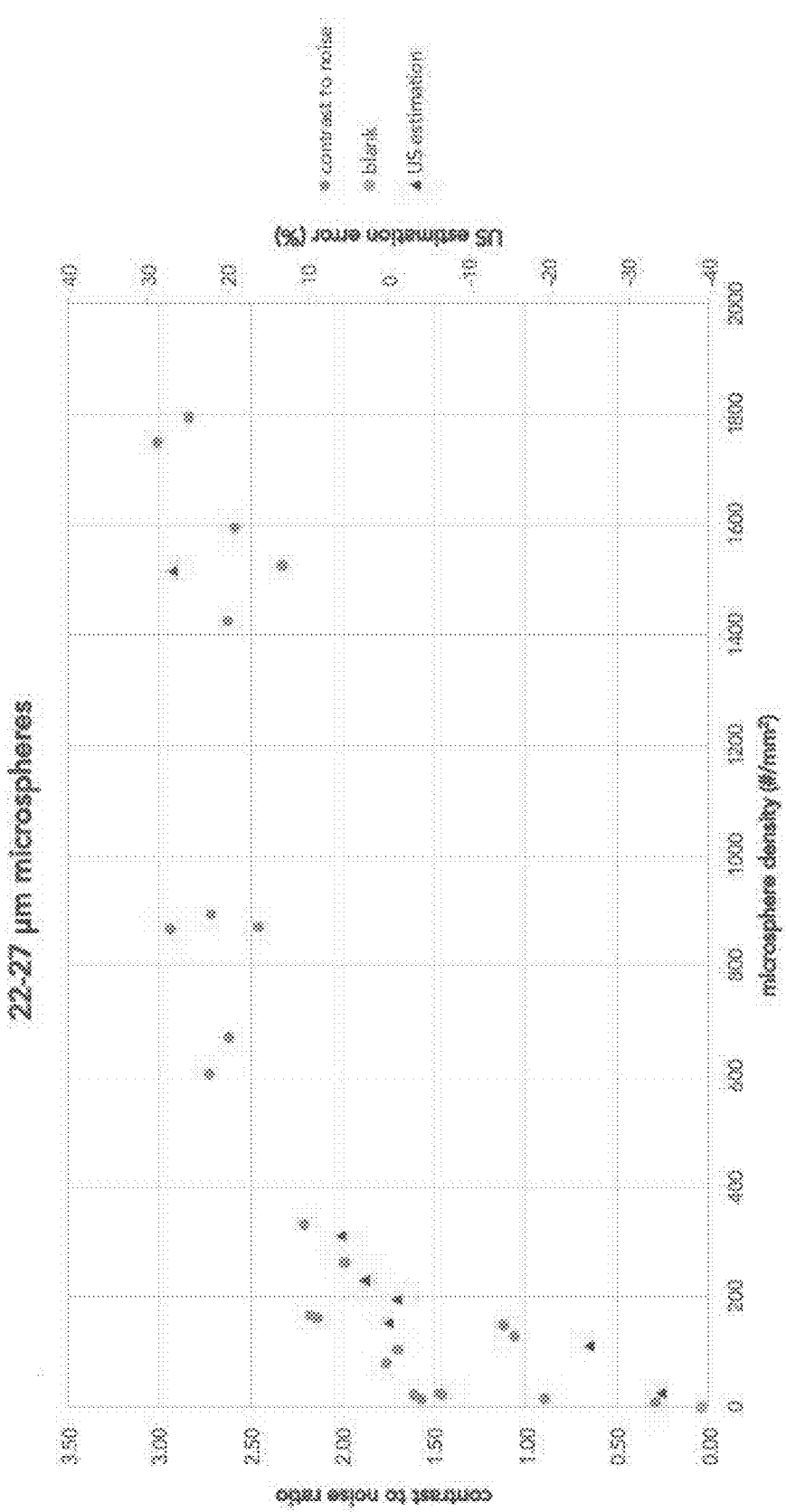
FIG. 2: For microspheres with a diameter between 22 and 27 μm, the CNR is plotted against the microsphere density, along with the US estimation error on the secondary y-axis.

In FIG. 2, for microspheres with a diameter between 22 and 27 μm, the CNR is plotted against the microsphere density, along with the US estimation error on the secondary y-axis. As can be seen in FIG. 2, the optimum range for these microspheres is lying between 150 and 450 particles/mm$^2$. Less microspheres on the surface leads to an underestimation of the width of the marker band, whereas above the upper limit, overestimation of the width occurs. The most optimal range for these microspheres is lying between 150 and 300 particles/mm$^2$.

In this fashion, the optimum microsphere density for each size range was established.

Figure 3:
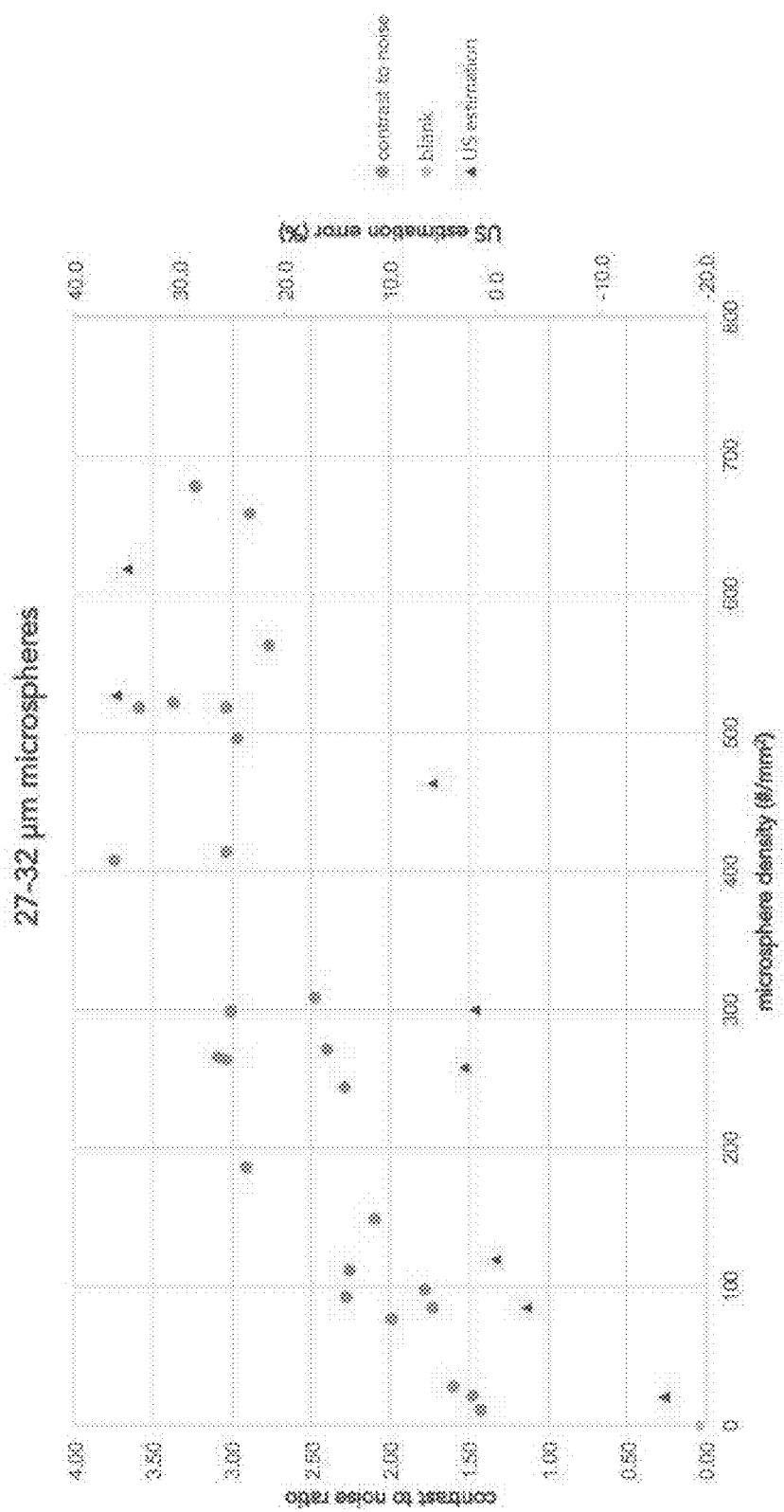
FIG. 3: For microspheres with a diameter between 27 and 32 μm, the CNR is plotted against the microsphere density, along with the US estimation error on the secondary y-axis.

In FIG. 3, for microspheres with a diameter between 27 and 32 μm, the CNR is plotted against the microsphere density, along with the US estimation error on the secondary y-axis. As can be seen in FIG. 3, the optimum range for these microspheres is lying between 70 and 450 particles/mm$^2$. Less microspheres on the surface leads to an underestimation of the width of the marker band, whereas above the upper limit, overestimation of the width occurs. A particular optimal range for these microspheres is lying between 80 and 300 particles/mm$^2$.

Figure 4:
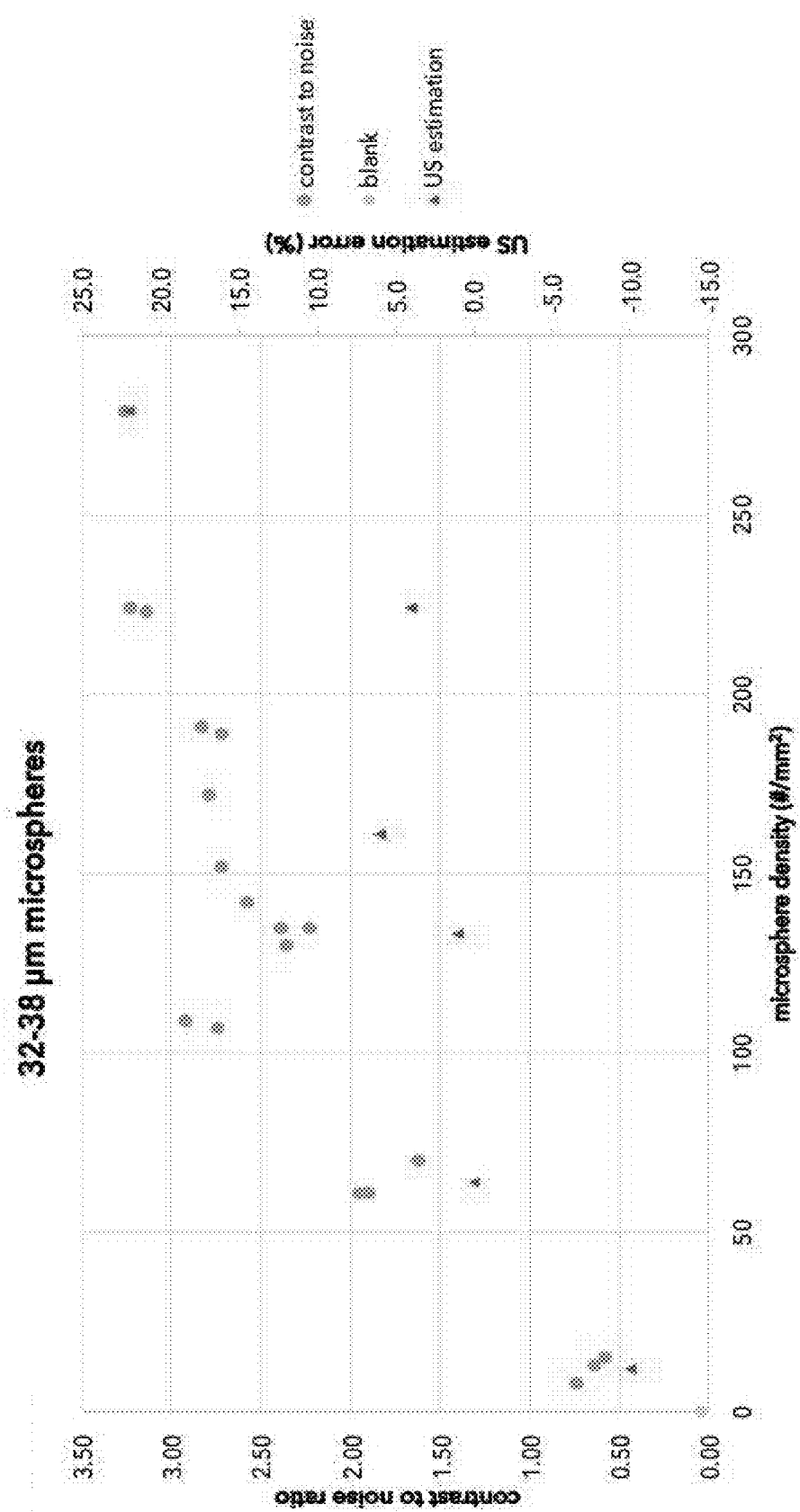
FIG. 4: For microspheres with a diameter between 32 and 38 μm, the CNR is plotted against the microsphere density, along with the US estimation error on the secondary y-axis.

In FIG. 4, for microspheres with a diameter between 32 and 38 μm, the CNR is plotted against the microsphere density, along with the US estimation error on the secondary y-axis. As can be seen in FIG. 4, the optimum range for these microspheres is lying between 45 and 225 particles/mm$^2$. Less microspheres on the surface leads to an underestimation of the width of the marker band, whereas above the upper limit, overestimation of the width occurs.

Figure 5:
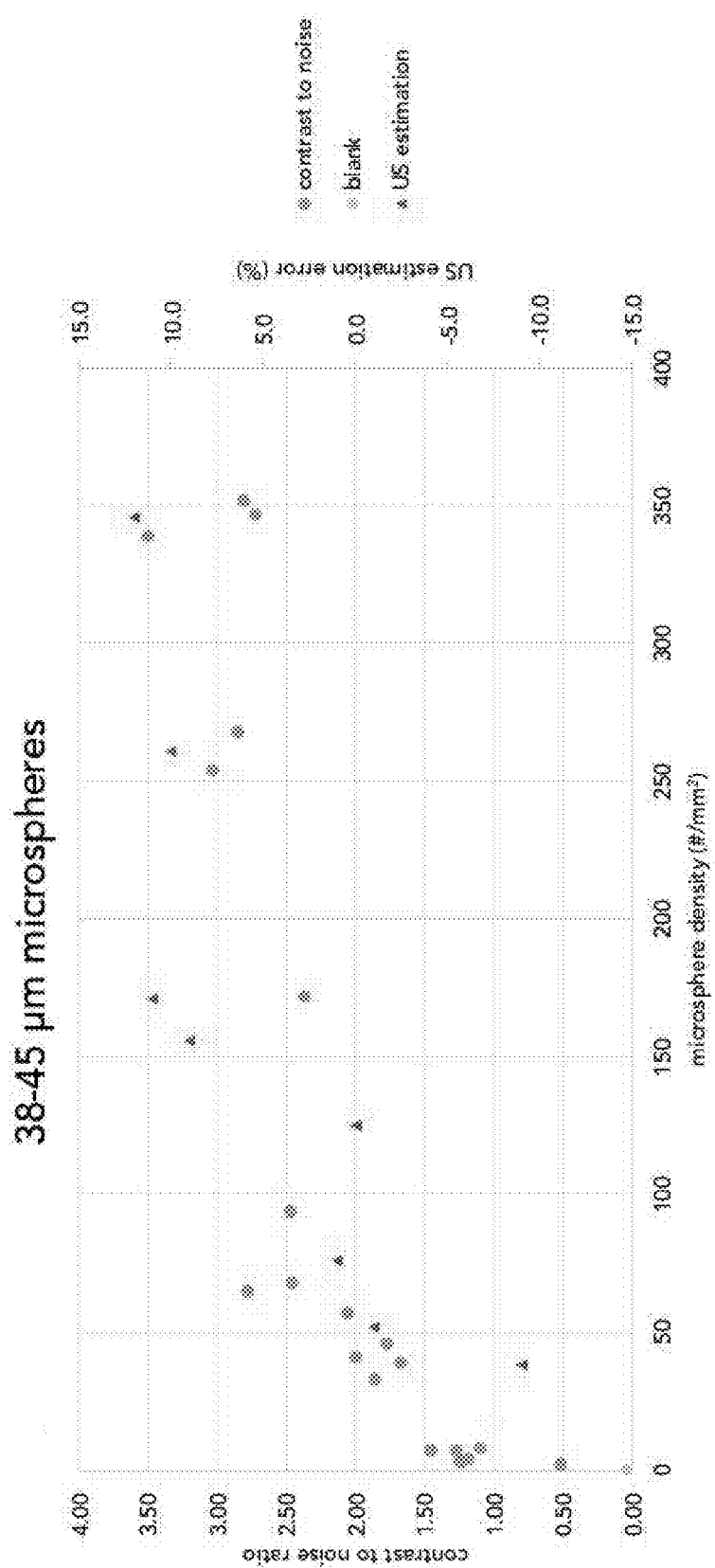
FIG. 5: For microspheres with a diameter between 38 and 45 μm, the CNR is plotted against the microsphere density, along with the US estimation error on the secondary y-axis.

In FIG. 5, for microspheres with a diameter between 38 and 45 μm, the CNR is plotted against the microsphere density, along with the US estimation error on the secondary y-axis. As can be seen in FIG. 5, the optimum range for these microspheres is lying between 45 and 150 particles/mm$^2$. Less microspheres on the surface leads to an underestimation of the width of the marker band, whereas above the upper limit, overestimation of the width occurs.

Figure 6:
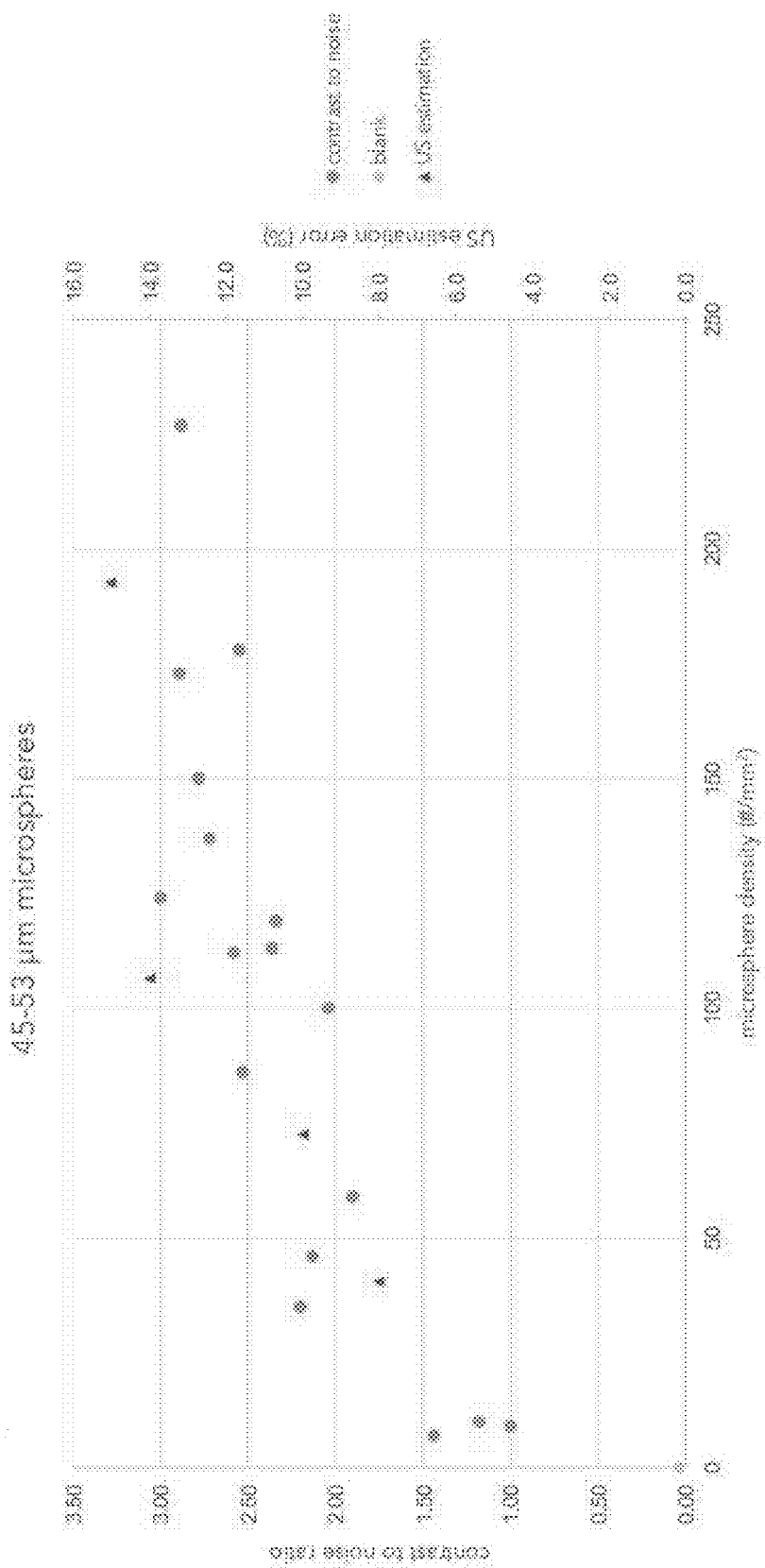
FIG. 6: For microspheres with a diameter between 45 and 53 μm, the CNR is plotted against the microsphere density, along with the US estimation error on the secondary y-axis.

For microspheres with diameters between 45 and 53 μm, on the other hand, no optimum particle density was found because overestimation of the width of the marker band is manifested over the complete range of particle density (FIG. 6).

Example 3

Solid glass microspheres with a diameter ranging from 38 to 45 μm, as described above, with a density of 2.5 g/mL, were mixed through a polyurethane coating matrix. Subsequently, glass slides and plastic (PEBAX® 6233) were coated with these particles in different densities. The coated substrates were measured by ultrasound using a 33-mm linear array probe operating in brightness-mode (B-mode) at 6 MHz. The substrates were placed under an approximate angle of 45 degrees inside a commercially available ultrasound phantom, which acted as the medium. From the recorded images, the contrast-to-noise ratio (CNR) was determined in the same way as described in Example 1, and the determined CNRs were plotted against the microsphere concentration (FIG. 7).

Figure 7:
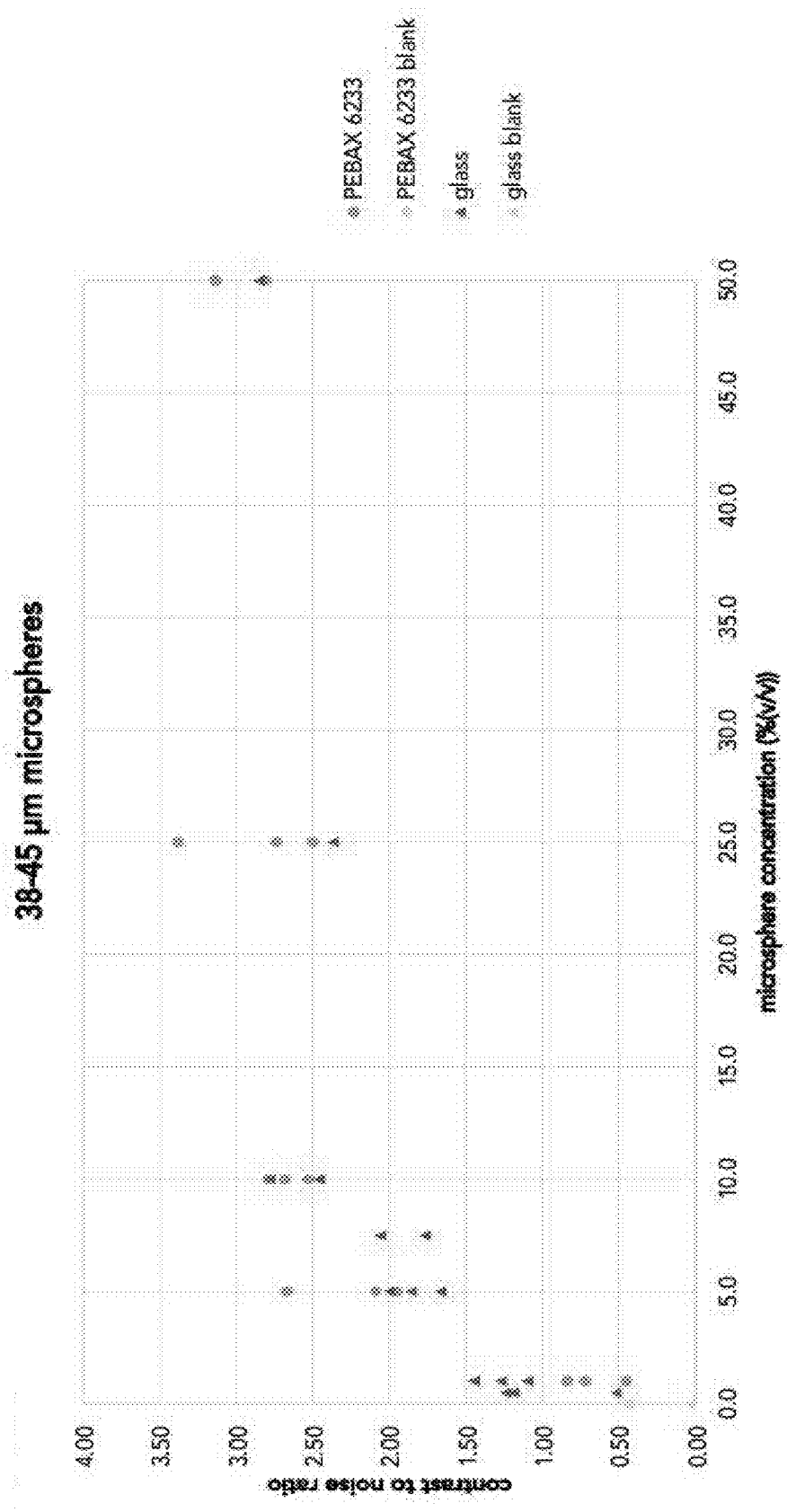
FIG. 7: CNR values for glass and plastic surfaces coated with solid glass microspheres with a diameter ranging from 38 to 45 μm.

As can be seen in FIG. 7, the CNR values for glass and plastic coated with the same amount of particles are comparable. This demonstrates that the material of the used surfaces does not significantly affect the CNRs.

Example 4

Example 1 was repeated with the solid glass microspheres with a diameter ranging from 22 to 27 μm, as described above, and with hollow glass microspheres with a diameter ranging from 25 to 27 μm and densities of 0.14 g/mL and 0.46 g/mL. Glass slides were coated with these particles in different densities. The coated substrates were measured by ultrasound using a 33-mm linear array probe operating in brightness-mode (B-mode) at 6 MHz. The substrates were placed under an approximate angle of 45 degrees inside a commercially available ultrasound phantom, which acted as the medium. From the recorded images, the contrast-to-noise ratio (CNR) was determined in the same way as described in Example 1, and the determined CNRs were plotted against the microsphere concentration (FIG. 8).

Figure 8:
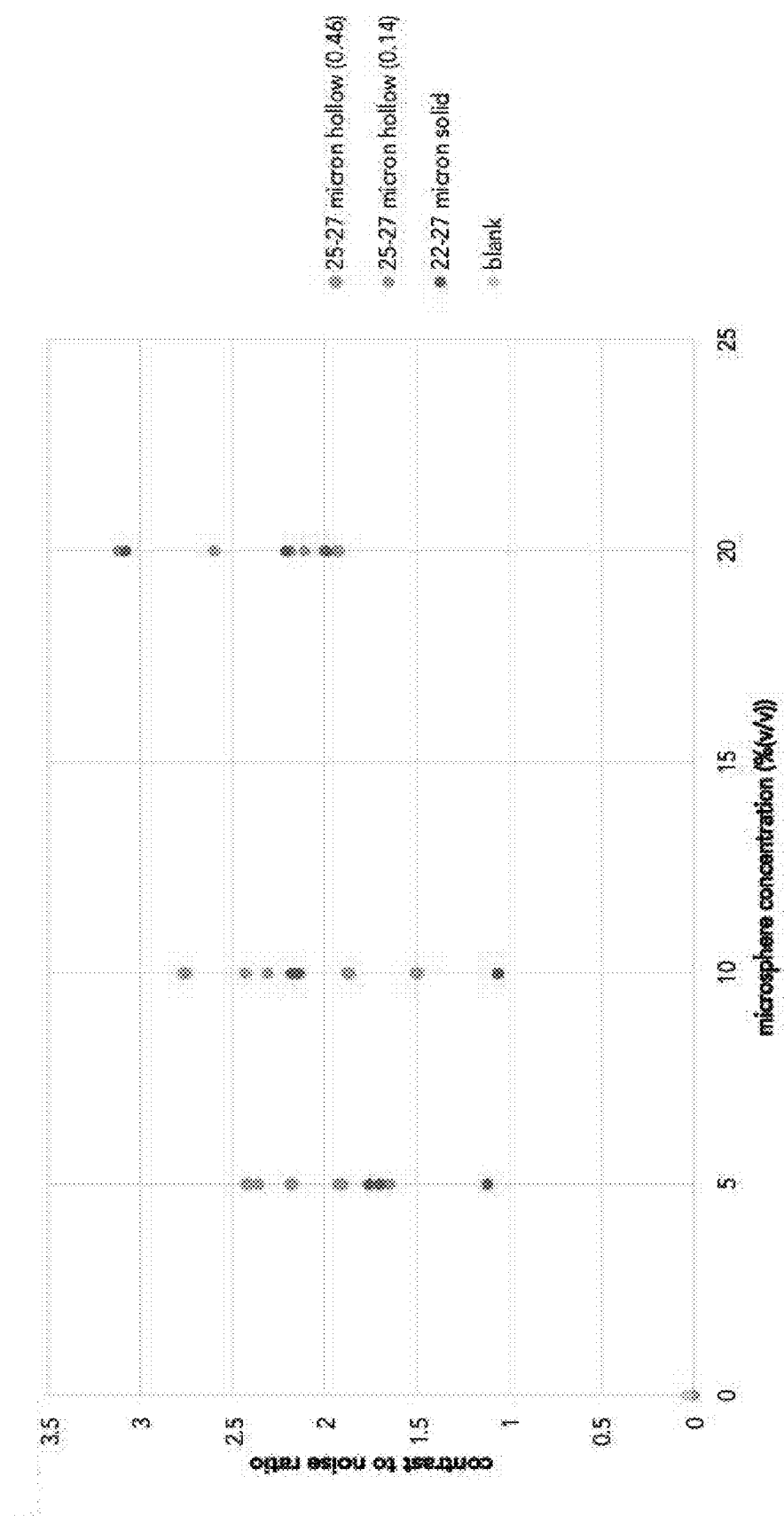
FIG. 8: CNR values for glass slides coated with solid glass microparticles and hollow glass microparticles.

As can be seen in FIG. 8, the CNR values for the solid and hollow particles are comparable, meaning that both solid and hollow particles are suitable for improving the visibility of a medical device according to this disclosure.

Example 5

Commercially available air-filled glass microspheres (from Cospheric) with diameters between 38 and 45 μm and a density of 0.46 g/mL were mixed through a coating matrix, Labo coat, which is commercially available from Labo Groep (Tilburg, The Netherlands). The microspheres were added in different amounts in order to prepare mixtures containing 2.0, 3.0 and 4.0 wt. % microspheres in the coating matrix. The coating was applied by dip coating on polyurethane tubes, resulting in coated tubes with a microsphere density of about 130 particles/mm$^2$ (image of Panel A of FIG. 9), about 180 particles/mm$^2$ (image of Panel B of FIG. 9), and about 250 particles/mm$^2$ (image of Panel C of FIG. 9), respectively.

The coated tubes were tested by ultrasound with a chicken breast as medium to record the images in.

Figure 9:
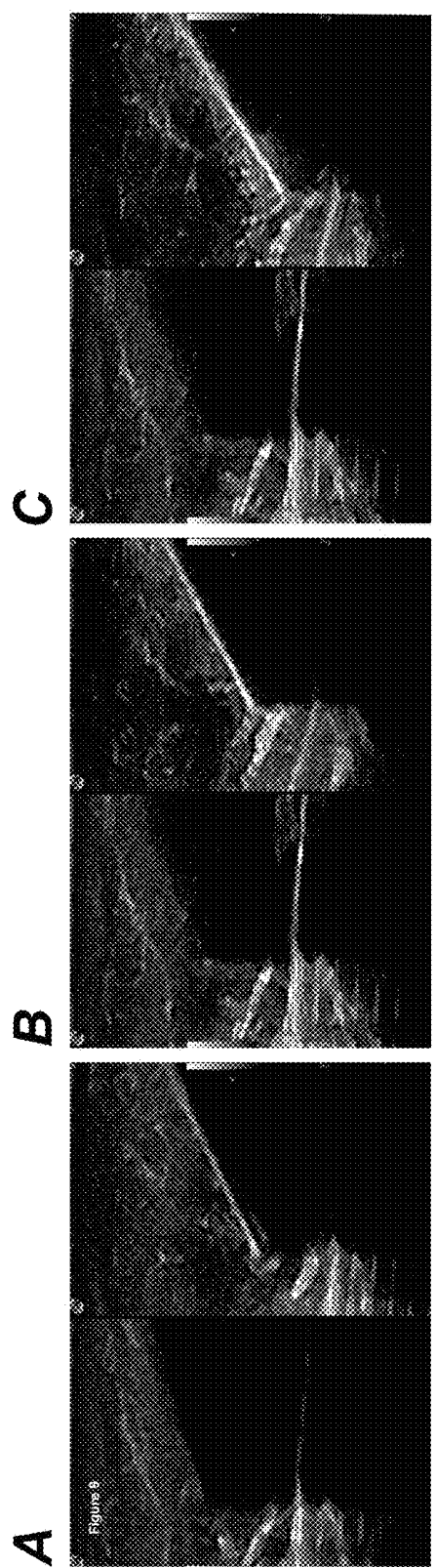
FIG. 9: Influence of the microsphere density on the surface. A microparticle density of lower than 250 particles/mm$^2$ on the surface of a medical device provides better ultrasound images than higher densities. (Panel A) Left image: hollow glass microspheres, surface density=about 130 particles/mm$^2$; (Panel B) Left image: hollow glass microspheres, surface density=about 180 particles/mm$^2$; (Panel C) Left image: hollow glass microspheres, surface density=about 250 particles/mm$^2$. Of note, the left part of each image shows a blank consisting of a chicken breast without tube; the right part of each image shows the results with a chicken breast with a coated tube.

Studying the different tubes with ultrasound showed that for higher amounts of microparticles on the surface, the surface of the tube starts to appear as rough, whereas at lower amounts, the surface appears to be smooth (see FIG. 9). At lower amounts, the visibility (sharpness of the image) improves.

Example 6

Solid glass microspheres with a diameter ranging from 38 to 45 μm, as described above in Example 1, were mixed through a polyurethane coating matrix. The microspheres were added in different amounts in order to prepare mixtures containing 1.0 to 75.0 vol. % microspheres in the coating matrix. Subsequently, either 30- or 60-μm thick marker bands of coating were drawn on glass slides using a film applicator. These marker bands were applied by masking the area that was required to be uncoated. The width of the marker bands was measured.

The coated substrates were measured by ultrasound using a 33-mm linear array probe operating in brightness-mode (B-mode) at 6 MHz. The substrates were placed under an approximate angle of 45 degrees inside a commercially available ultrasound phantom, which acted as the medium.

Figure 10:
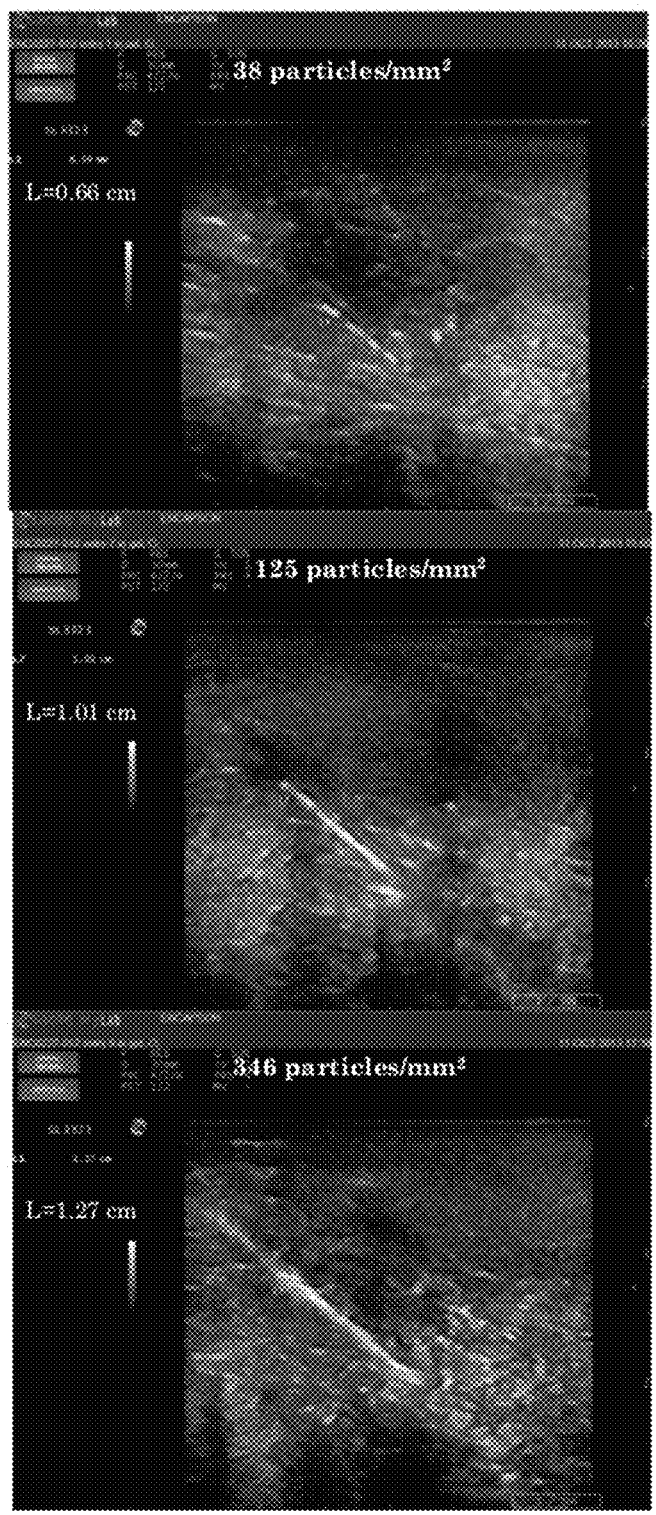
FIG. 10: Ultrasound images taken in a phantom gel of glass slides on which marker bands (width 1 cm) were applied of Sono-Coat comprising different concentrations of microspheres (size range 38-45 μm).

FIG. 10 shows ultrasound images taken in a phantom gel of glass slides on which marker bands (width 1 cm) were applied of Sono-Coat comprising the microspheres (size range 38-45 μm) in a concentration of 38 particles/mm², 125 particles/mm², and 346 particles/mm². It is clear that the middle image, which is within the density range of 45-150 particles/mm² according to the disclosure, provides the best visibility combined with an accurate measurement of the width of the marker band. The lower image (density of 346 particles/mm²) is more vague and overestimation of the marker band width occurs, whereas the upper image is also more vague, appears as a dotted line, and underestimates the width of the marker band.

Example 7

Figure 11:
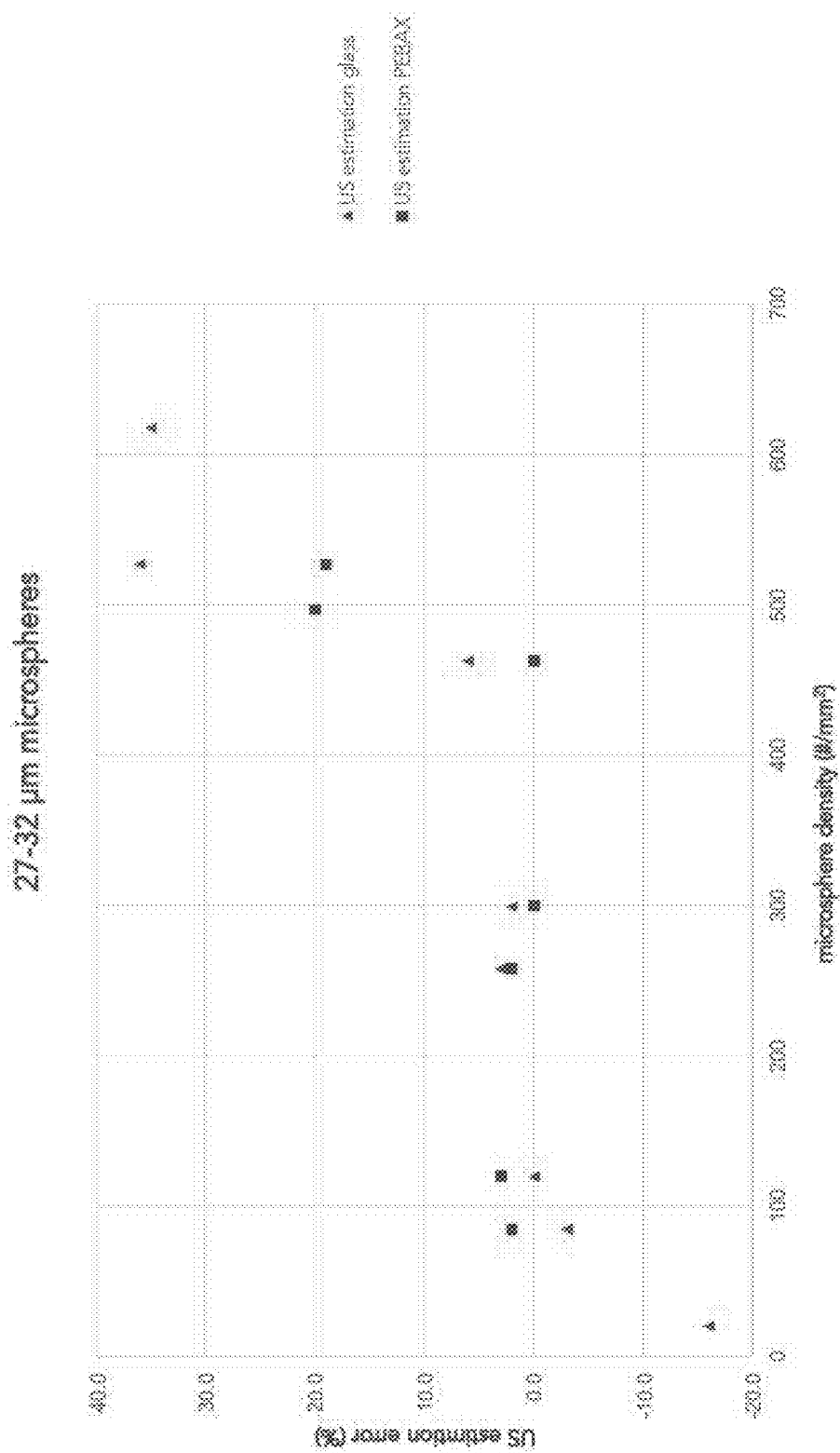
FIG. 11: US estimation error plotted against the microsphere density on glass and plastic surfaces coated with microspheres with a diameter between 27-32 μm.

The same kind of experiment as Example 2 was repeated. The same kind of 27-32 μm microspheres were used. These microspheres were coated on glass slides as well as on plastic (PEBAX®) surfaces. In FIG. 11, the US estimation error is plotted against the microsphere density. From FIG. 11, it is clear that the optimum microsphere density range is the same for both the coated glass and the coated plastic surfaces. Like in FIG. 3, the optimum range for these microspheres is between 70 and 450 particles/mm². Hence, the visibility is dependent upon the scattering effect of the coating, not the surface itself.

REFERENCES

Baldelli et al., *Eur. Radiol.* 19 (2009); 2275-2285.
Couture et al., *Ultrasound in Medicine and Biology*, Vol. 32, No. 8, pp. 1247-1255, 2006.
Song et al., *Applied Optics*, Vol. 43, No. 5 (2004); 1053-1062.
EP Patent 0624342
EP Patent 1118337
U.S. Pat. No. 5,081,997
U.S. Pat. No. 5,289,831
U.S. Pat. No. 5,921,933
U.S. Pat. No. 6,506,156
U.S. Patent Publication 2004/0077948
U.S. Patent Publication 2005/0074406
U.S. Patent Publication 2009/0318746
International Patent Publication WO 98/18387
International Patent Publication WO 00/51136
International Patent Publication WO 00/66004
International Patent Publication WO 2007/089761

The invention claimed is:

1. A medical device comprising a coating for ultrasound detection, said coating comprising microspheres that are visible with ultrasound, wherein the microspheres are solid and wherein the microspheres comprise glass or silicate, and wherein the diameter of at least 60% of said microspheres on said medical device is between 22 and 45 μm and wherein the density of said microspheres on the surface of said medical device is between 45 and 450 microspheres/mm², wherein one of the following conditions a)-d) is met:
a) the diameter of at least 60% of the microspheres on the medical device is between 22 and 27 μm and the density of the microspheres on the surface of the medical device is between 150 and 450 microspheres/mm², or
b) the diameter of at least 60% of the microspheres on the medical device is between 27 and 32 μm and the density of the microspheres on the surface of the medical device is between 70 and 450 microspheres/mm², or
c) the diameter of at least 60% of the microspheres on the medical device is between 32 and 38 μm and the density of the microspheres on the surface of the medical device is between 45 and 225 microspheres/mm², or
d) the diameter of at least 60% of the microspheres on the medical device is between 38 and 45 μm and the density of the microspheres on the surface of the medical device is between 45 and 150 microspheres/mm².

2. The medical device of claim 1, wherein said coating comprises a matrix material selected from the group of polymers consisting of a poly(ether sulfone); a polyisocyanate; a polyurethane; a polytetrafluoroethylene; a polymer of N-vinyl-pyrrolidone, a copolymer of N-vinyl-pyrrolidone, a copolymer with butylacrylate; a poly(4-vinyl pyridine); a polyacrylamide, poly(N-isopropylacrylamide); a poly(amido-amine); a poly(ethylene imine); a polymer of ethylene oxide and propylene oxide, a block copolymer of ethylene oxide and propylene oxide, a poly(ethylene oxide-block-propylene oxide), a poly(ethylene oxide-block-propylene oxide-block-ethylene oxide); a block copolymer, a block styrene, poly(styrene-block-isobutylene-block-styrene), a poly(hydroxystyrene-block-isobutylene-block-hydroxystyrene); a polydialkylsiloxane; a polysaccharide; a polystyrene, a polyacrylate; a polyalkane, polyethylene, polypropylene, polybutadiene; a poly(ether ketone), a poly(ether ether ketone); a polyester, poly(ethylene terephthalate), polyglycolide, poly(trimethylene terephthalate), poly(ethylene naphthalate), polylactic acid), polycapralactone, poly(butylene terephthalate); polyamides, nylon-6,6, nylon-6, polyphthalamides, polyaramides; a polymethylmethacrylate, a poly(2-hydroxyethylmethacrylate); poly(ether sulfones), polyurethanes, polyacrylates, polymethacrylates, polyamides, polyisocyanates and combinations of any thereof.

3. The medical device of claim 1, wherein said medical device is selected from the group consisting of a catheter, a needle, a stent, a cannula, a tracheotome, an endoscope, a dilator, a tube, an introducer, a marker, a stylet, a snare, an angioplasty device, a fiducial, a trocar and a forceps.

4. A method for preparing the medical device of claim 1, the method comprising:
providing a medical device, and
coating said medical device with microspheres that are solid and comprise glass or silicate and that are visible with ultrasound, such that the diameter of at least 60% of said microspheres on said medical device is between 22 and 45 μm and the density of said microspheres on the surface of said medical device is between 45 and 450 microspheres/mm², wherein one of the following conditions a)-d) is met:
a) the diameter of at least 60% of the microspheres on the medical device is between 22 and 27 μm and the density of the microspheres on the surface of the medical device is between 150 and 450 microspheres/mm², or
b) the diameter of at least 60% of the microspheres on the medical device is between 27 and 32 μm and the density of the microspheres on the surface of the medical device is between 70 and 450 microspheres/mm², or
c) the diameter of at least 60% of the microspheres on the medical device is between 32 and 38 μm and the density of the microspheres on the surface of the medical device is between 45 and 225 microspheres/mm², or d) the diameter of at least 60% of said microspheres on the medical device is between 38 and 45 µm and the density of the microspheres on the surface of the medical device is between 45 and 150 microspheres/mm$^2$.

5. The method of claim 4, wherein the coating comprises a matrix material selected from the group consisting of a poly(ether sulfone), a polyisocyanate, a polyurethane, a polytetrafluoroethylene, a polymer of N-vinyl-pyrrolidone, a copolymer of N-vinyl-pyrrolidone, a copolymer with butylacrylate, a poly(4-vinyl pyridine), a polyacrylamide, poly(N-isopropylacrylamide), a poly(amido-amine), a poly(ethylene imine), a polymer of ethylene oxide and propylene oxide, a block copolymer of ethylene oxide and propylene oxide, a poly(ethylene oxide-block-propylene oxide), a poly(ethylene oxide-block-propylene oxide-block-ethylene oxide), a block copolymer, a block styrene, poly(styrene-block-isobutylene-block-styrene), a poly(hydroxystyrene-block-isobutylene-block-hydroxystyrene), a polydialkylsiloxane, a polysaccharide, a polystyrene, a polyacrylate, a polyalkane, polyethylene, polypropylene, polybutadiene, a poly(ether ketone), a poly(ether ether ketone), a polyester, a poly(ethylene terephthalate), a polyglycolide, a poly(trimethylene terephthalate), a poly(ethylene naphthalate), a poly(lactic acid), a polycapralactone, a poly(butylene terephthalate), polyamides, nylon-6,6, nylon-6, polyphthalamides, polyaramides, a polymethylmethacrylate, a poly(2-hydroxyethylmethacrylate), poly(ether sulfones), polyurethanes, polyacrylates, polymethacrylates, polyamides, polyisocyanates and combinations of any thereof.

6. The method of claim 4, wherein the medical device is selected from the group consisting of a catheter, a needle, a stent, a cannula, a tracheotome, an endoscope, a dilator, a tube, an introducer, a marker, a stylet, a snare, an angioplasty device, a fiducial, a trocar and a forceps.

* * * * *